(12) United States Patent
Atwell

(10) Patent No.: US 9,820,805 B2
(45) Date of Patent: Nov. 21, 2017

(54) ELECTROSURGICAL INSTRUMENT AND SYSTEM

(71) Applicant: GYRUS MEDICAL LIMITED, Cardiff (GB)

(72) Inventor: Anthony K. Atwell, Newport (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 215 days.

(21) Appl. No.: 14/404,582

(22) PCT Filed: Jun. 6, 2013

(86) PCT No.: PCT/GB2013/051491
§ 371 (c)(1),
(2) Date: Nov. 28, 2014

(87) PCT Pub. No.: WO2013/186533
PCT Pub. Date: Dec. 19, 2013

(65) Prior Publication Data

US 2015/0209099 A1    Jul. 30, 2015

(30) Foreign Application Priority Data

Jun. 12, 2012 (GB) .................................. 1210296.8

(51) Int. Cl.
*A61B 18/14* (2006.01)
*A61B 17/00* (2006.01)
(Continued)

(52) U.S. Cl.
CPC ...... *A61B 18/1402* (2013.01); *A61B 18/1445* (2013.01); *A61B 18/1477* (2013.01);
(Continued)

(58) Field of Classification Search
CPC .... A61B 2018/1226; A61B 2018/1286; A61B 2018/0091; A61B 2018/00172;
(Continued)

(56) References Cited

U.S. PATENT DOCUMENTS 4,244,371 A * 1/1981 Farin .................. A61B 18/1233
606/34
4,878,493 A   11/1989 Pasternak et al.
(Continued)

FOREIGN PATENT DOCUMENTS

CN    102 16 4557 A    8/2011
CN    102 11 2067 A    11/2013
(Continued)

OTHER PUBLICATIONS

English Translation of Chinese Office Action dated May 30, 2016 in corresponding Chinese Application No. 201380029275.1.
(Continued)

*Primary Examiner* — Jaymi Dela
*Assistant Examiner* — Eunhwa Kim
(74) *Attorney, Agent, or Firm* — Nixon & Vanderhye PC

(57) ABSTRACT

A handheld electrosurgical instrument includes a handpiece (2) and an electrode assembly (3), the electrode assembly including one or more electrodes (12), (13) and a connector (8), (9) by which the electrode assembly (3) is capable of being attached and detached with respect to the handpiece (2). The handpiece includes a battery (4), an RF oscillator circuit (5) for generating a radio frequency output, and switching means (7) operable by a user of the electrosurgical instrument. A control circuit is provided (6) for controlling the RF output, the control circuit (6) being capable of receiving signals from the switching means (7) and causing one or more RF outputs to be supplied to the electrode assembly (3) in response thereto. The electrode assembly (3)

(Continued)

includes a component (14), (21) capable of modifying the RF output reaching the one or more electrodes (12), (13) to produce a desired RF output at the one or more electrodes.

4 Claims, 3 Drawing Sheets

(51) Int. Cl.
   *A61B 18/00* (2006.01)
   *A61B 18/12* (2006.01)
(52) U.S. Cl.
   CPC .............. *A61B 2017/00477* (2013.01); *A61B 2018/0091* (2013.01); *A61B 2018/00172* (2013.01); *A61B 2018/00178* (2013.01); *A61B 2018/1226* (2013.01); *A61B 2018/1286* (2013.01); *A61B 2018/1425* (2013.01); *A61B 2018/1495* (2013.01)
(58) Field of Classification Search
   CPC .. A61B 2018/00178; A61B 2018/1495; A61N 1/37211; A61N 1/37223; A61N 1/40
   See application file for complete search history.

(56) References Cited

U.S. PATENT DOCUMENTS

| | | | |
|---|---|---|---|
| 5,817,092 A | 10/1998 | Behl | |
| 6,391,025 B1 | 5/2002 | Weinstein et al. | |
| 2003/0088245 A1* | 5/2003 | Woloszko | A61B 18/148 606/41 |
| 2004/0111087 A1 | 6/2004 | Stern et al. | |
| 2007/0016182 A1* | 1/2007 | Lipson | A61B 18/12 606/34 |
| 2010/0036371 A1 | 2/2010 | Park et al. | |
| 2010/0082026 A1 | 4/2010 | Curtis | |
| 2010/0094288 A1 | 4/2010 | Kerr | |
| 2011/0251606 A1* | 10/2011 | Kerr | A61B 18/1402 606/34 |

FOREIGN PATENT DOCUMENTS

| | | |
|---|---|---|
| GB | 1454773 | 11/1976 |
| GB | 2480498 | 11/2011 |
| WO | WO 97/24073 | 7/1997 |
| WO | WO 99/01074 | 1/1999 |
| WO | WO 2004/080278 | 9/2004 |

OTHER PUBLICATIONS

First Office Action dated May 30, 2016 in corresponding Chinese Application No. 201380029275.1.
International Search Report for PCT/GB2013/051491 dated Nov. 7, 2013.
Written Opinion of the International Searching Authority for PCT/GB2013/051491 dated Nov. 7, 2013.
Search Report for GB 1210296.9 dated Oct. 10, 2012.

* cited by examiner

ELECTROSURGICAL INSTRUMENT AND SYSTEM

This application is the U.S. national phase of International Application No. PCT/GB2013/051491 filed 6 Jun. 2013 which designated the U.S. and claims priority to GB 1210296.8 filed 12 Jun. 2012, the entire contents of each of which are hereby incorporated by reference.

TECHNICAL FIELD

This invention relates to an electrosurgical instrument and to an electrosurgical system for use in the treatment of tissue. Such systems are used in endoscopic or "keyhole" surgery, as well as more traditional "open" surgery.

BACKGROUND TO THE INVENTION AND PRIOR ART

Many electrosurgical systems have some form of identification system, such that when an electrosurgical instrument is connected to an electrosurgical generator, the generator is able to detect which type of instrument is present, and even use settings such as power and voltage settings which are appropriate for that particular instrument or type of instrument. Our U.S. Pat. No. 6,074,386 is one example of such an identification system, although other types are also known.

SUMMARY OF THE INVENTION

The present invention attempts to provide an alternative to such identification systems, such that the generator used as part of the electrosurgical system can be substantially simplified, which is particularly important when attempting to provide a handheld electrosurgical instrument. Accordingly, a handheld electrosurgical instrument comprises a handpiece and an electrode assembly, the electrode assembly including one or more electrodes and a connector by which the electrode assembly is capable of being attached and detached with respect to the handpiece, the handpiece including, a) a battery;
b) an RF oscillator circuit for generating a radio frequency output;
c) a switching means operable by a user of the electrosurgical instrument; and
d) a control circuit for controlling the RF output, the control circuit being capable of receiving signals from the switching means and causing one or more RF outputs to be supplied to the electrode assembly in response thereto;
wherein the electrode assembly includes a component capable of taking the RF output exiting the handpiece and modifying it such that the RF output reaching the one or more electrodes is different from that exiting the handpiece.

By including the modifying component in the electrode assembly, the control circuit in the handpiece can be simplified, such that the control circuit does not need to include circuitry to produce a wide range of different RF outputs. The modifying component is able to customise the electrosurgical output from the handpiece before it is passed on to the electrode assembly. In this way, the output of the handpiece is customised in order to produce an output at the electrode assembly which is suitable for the particular circumstances, depending on the type of instrument and the particular procedure to be carried out.

As previously stated, the handpiece does not need to be capable of producing a wide range of electrosurgical outputs to cover various electrode assemblies and procedures. The handpiece merely produces basic electrosurgical outputs, which are modified by the modifying component in the electrode assembly to produce the selected output. Conceivably, the handpiece is so simple that it produces a single RF output whenever activated, with the electrode assembly modifying the RF output to produce the desired RF output at the one or more electrodes.

In a convenient arrangement, the component capable of modifying the RF output reaching the one or more electrodes comprises a transformer including at least a primary winding and a secondary winding. Alternatively, the handpiece includes a primary transformer winding, and the electrode assembly includes a secondary transformer winding, such that when the electrode assembly is connected to the handpiece the primary and secondary windings are connected in order to act as a transformer to modify the radio frequency output from the RF oscillator circuit. In this way, even if the handpiece is only capable of producing a single RF output, the secondary winding modifies the output in order to produce an electrosurgical output suitable for the electrode assembly concerned. It will be appreciated that the handpiece can be employed in connection with a variety of different electrode assemblies, either having different electrodes, or being intended for different electrosurgical procedures. Each type of electrode assembly will be provided with secondary windings consisting of a particular number of turns, so as to modify the output of the handpiece to render it suitable for that particular electrode assembly.

In a convenient arrangement, the electrode assembly includes a passive electrical component having a parameter of a finite non-zero value, the passive electrical component being such as to modify the RF output reaching the one or more electrodes to produce a desired RF output at the one or more electrodes. Conveniently, the passive electrical component acts in combination with the control circuit in order to modify the RF output reaching the one or more electrodes. The passive electrical component is typically a resistor, or other impedance, although reactive components such as capacitors or inductors may be used, depending on the transformation required from the signal supplied by the handpiece to the signal required by the end-effector. Moreover, networks of components may be used to provide the appropriate transfer function.

For a first type of electrode assembly (say, for instance, a cutting needle), the value of the resistor is such as to modify or control the output of the handheld instrument so as to produce a suitable cutting voltage. For a second type of electrode assembly (say, for instance, a pair of coagulating jaws), the value of the resistor is different, so as to produce a different output more suited to the coagulation of tissue.

The modifying component present in the electrode assembly is conveniently capable of modifying any one or more of a plurality of parameters associated with the output from the handpiece, including the power, voltage or current of the RF energy, the frequency of the RF energy, or the format (continuous or pulsed bursts) of the RF energy. By placing this capability in the electrode assembly, the handpiece can be substantially simplified in construction and design.

From another aspect an embodiment of the invention provides an electrosurgical instrument comprising a handpiece and an electrode assembly releasably connectable to the handpiece, the handpiece comprising: an RF signal source; and a control switch operable by the user to control the handpiece to output a radio frequency (RF) signal derived from the RF signal source; the electrode assembly comprising: one or more electrodes forming an end effector for the treatment of tissue when an RF treatment signal is applied thereto; and circuitry arranged to receive the radio frequency signal from the handpiece and to convert it into the RF treatment signal required by the end effector. With the above arrangement then as described previously the handpiece can be of a very simple design, as it is not required to produce different waveforms. Instead, the specific waveform production is left to componentry in the electrode assembly, which is adapted to convert the general or standard waveform received from the handpiece to the specific waveform required by the specific type of end effector in the electrode assembly.

For example, the RF treatment signal produced by the componentry in the electrode assembly is a RF cutting signal when the end effector is a cutting instrument, or a RF coagulation signal when the end effector is a coagulation instrument.

In one embodiment the circuitry comprises at least the secondary coil of a transformer, arranged to alter the RF signal output from the handpiece. In particular, the handpiece may comprise a primary coil of the transformer, the primary coil arranged to receive a signal from the RF signal source and to generate the output RF signal from the handpiece. In this way the handpiece and the electrode assembly together cooperate to produce the RF treatment signal from the RF signal source.

In an alternative embodiment, the circuitry further comprises a primary coil of the transformer, the primary coil arranged to receive the output RF signal from the handpiece. In such an embodiment all of the signal conversion from the general or standard waveform to the RF treatment is undertaken in the electrode assembly.

In one embodiment the circuitry comprises an electrical network arranged to convert the radio frequency signal to the RF treatment signal. Preferably the electrical network is a passive network comprising one or more resistances, impedances and/or reactances. Passive networks are simpler to implement and operate.

The invention further resides in an electrosurgical system comprising a handpiece and a plurality of electrode assemblies, the electrode assemblies being at least of a first type or a second type of electrode assembly, and each including one or more electrodes and being detachably connectible to the handpiece, the handpiece comprising a) a battery;
b) an RF oscillator circuit for generating a radio frequency output;
c) a switching means operable by a user of the electrosurgical instrument; and
d) a control circuit for controlling the RF output, the control circuit being capable of receiving signals from the switching means and causing one or more RF outputs to be supplied to the electrode assembly in response thereto;

wherein the first type of electrode assembly includes a first component and the second type of electrode assembly includes a second component, the first and second components being capable of taking the RF output exiting the handpiece and modifying it such that the RF output reaching the one or more electrodes of the first type of electrode assembly is different from the RF output reaching the one or more electrodes of the second type of electrode assembly.

BRIEF DESCRIPTION OF THE DRAWINGS

The invention will now be described in more detail, by way of example only, with reference to the accompanying drawings, in which.

DESCRIPTION OF EMBODIMENTS

Figure 1:
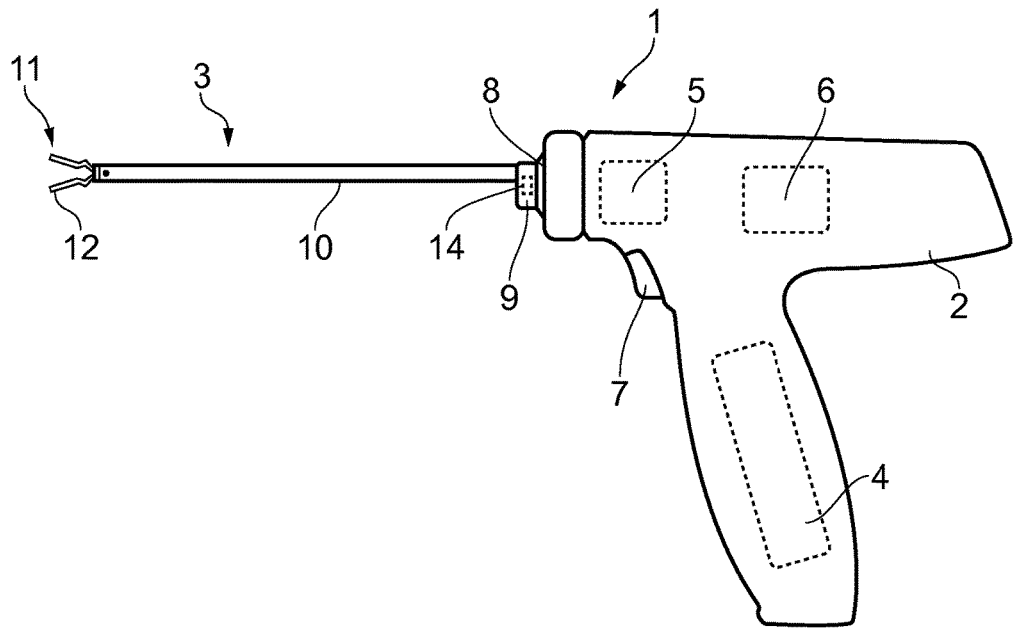
FIGS. 1 & 2 are schematic diagrams of handheld electrosurgical instruments in accordance with the present invention.

FIG. 1 shows a handheld electrosurgical instrument shown generally at 1, and comprising a handpiece 2 and an electrode assembly 3. The handpiece 2 includes a power source such as battery 4, RF circuit 5 and control circuit 6. The handpiece is provided with a handswitch 7 for giving instructions to the control circuit 6. The handpiece includes a handpiece connector 8 mating with a corresponding electrode assembly connector 9 carried by the electrode assembly 3. The electrode assembly includes an elongate shaft 10 and an end effector 11 at the distal end of the shaft. In FIG. 1, the electrode assembly is such that the end effector 11 comprises a pair of jaws 12. Leads (not shown) run along the shaft 10 of the electrode assembly 3 to connect the RF circuit to the end effector 11, such that the jaws 12 constitute electrodes capable of the coagulation of tissue.

Figure 2:
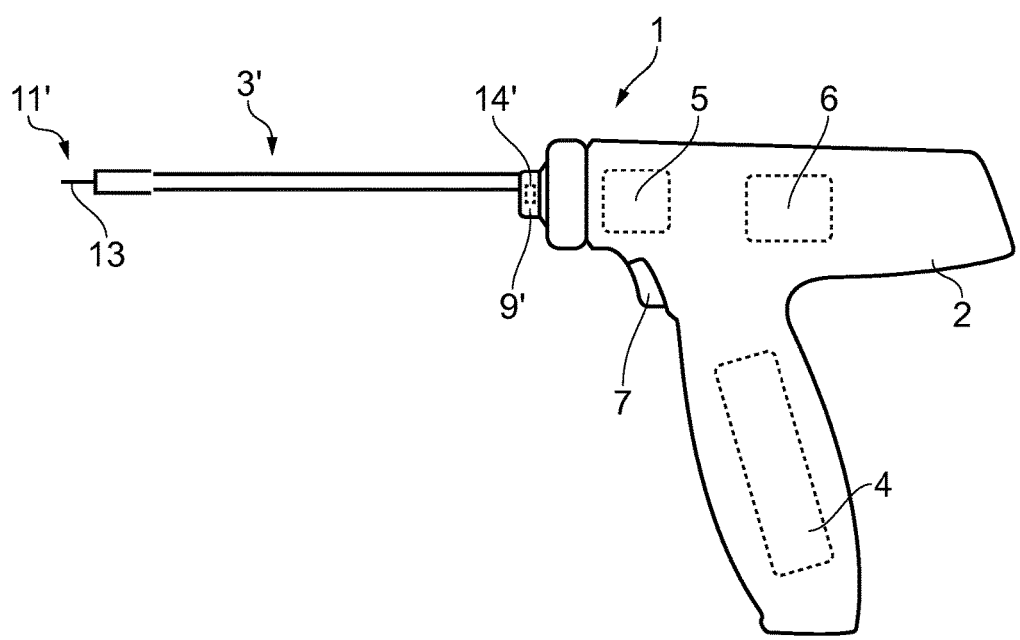

FIG. 2 shows the handpiece 2 together with a different electrode assembly 3'. The electrode assembly 3' has a connector 9' and is such that its end effector 11' comprises a deployable cutting needle 13. Once again, leads (not shown) run along the shaft 10' of the electrode assembly 3' to connect the RF circuit to end effector 11', such that the cutting needle 13 constitutes an electrode capable of the cutting of tissue. Hence, as is known in the art both cutting and coagulation of tissue is possible, dependent upon the end effector design, and the characteristics of the RF signal supplied to the end effector, such as the power and frequency of the RF signal.

The connector 9 on the electrode assembly 3 includes a resistor 14, which becomes part of the RF circuit 5 when the electrode assembly 3 is connected to the handpiece 2. The resistor 14 in the electrode assembly 3 of FIG. 1 has a different value to the resistor 14' in the electrode assembly 3' of FIG. 2. This means that when the handswitch 7 is used to activate the instrument of FIG. 1, the resistor 14 modifies the RF output reaching the jaws 12 so as to make the RF output suitable for the coagulation of tissue. In contrast, when the handswitch 7 is used to activate the instrument of FIG. 2, the resistor 14' modifies the RF output reaching the cutting needle 13 so as to make the RF output suitable for the cutting of tissue. This change is not carried out within the handpiece 2, which can if necessary produce the same RF output in both occasions. Instead, it is the resistors 14 & 14' that modify the output in order to make it suitable for each respective use of the instrument. This keeps the design of the handpiece as simple as possible, which is very advantageous for a handheld instrument in which both weight and cost are serious considerations.

Figure 3:
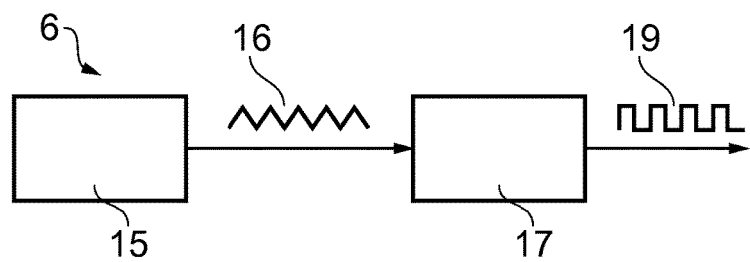
FIG. 3 is a schematic diagram of the control circuit of the handheld electrosurgical instruments of FIGS. 1 & 2, FIGS. 4 & 5 are diagrams of the waveforms produced by the control circuit of FIG. 3, and FIGS. 6A & 6B are schematic diagrams of primary and secondary windings forming components of the handheld surgical instruments of FIGS. 1 & 2.
Figure 4:
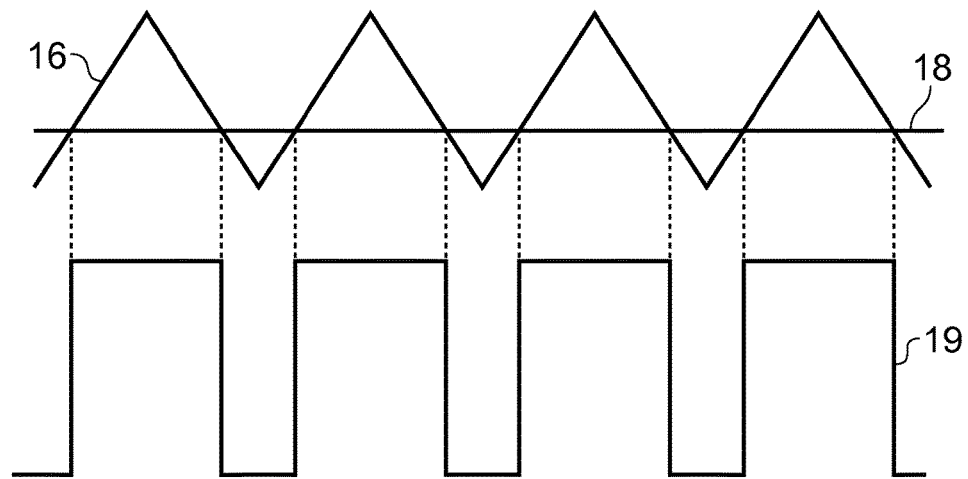

FIG. 3 shows the control circuit 6 for the RF circuit 5. The control circuit includes a signal generator 15 generating a saw-tooth waveform 16, typically produced by the integration of the amplified current signal. This saw-tooth waveform is input to a comparator 17, the output of which is used to control the RF circuit 5. FIG. 4 shows the action of the comparator 17, in which the saw-tooth waveform 16 is compared to a threshold voltage 18. The threshold voltage is set by a circuit such as a potential divider completed by the resistor 14, such that the level of the threshold voltage 18 is dependent on the value of the resistor 14. FIG. 4 shows how the saw-tooth waveform 16 is compared to the threshold 18 to generate a square wave 19 the mark to space ratio (or duty cycle) of which is set by the threshold 18. This square wave 19 is used to control the RF circuit, the RF circuit being "on" when the square wave is high and "off" when the square wave is low. Thus the power of the RF energy supplied to the electrode assembly 3 is dependent on the mark to space ratio (duty cycle) of the square wave 19, and hence the resistor 14.

Figure 5:
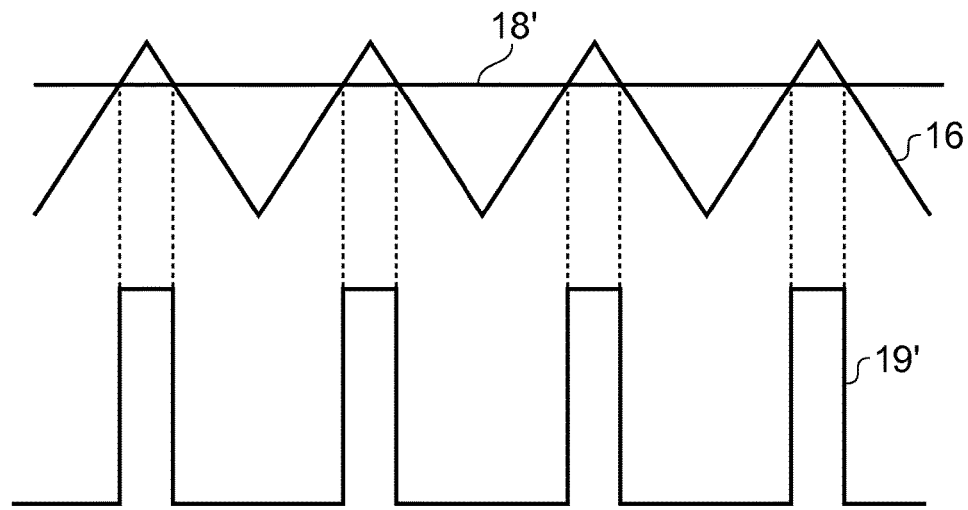

FIG. 5 shows the action of a higher value resistor 14' resulting in a higher threshold 18' The comparator produces a square wave 19' similar to that of FIG. 4, but with a much smaller mark to space ratio (duty cycle). Thus, the power of the RF energy supplied to the electrode assembly 3' is reduced compared to that of electrode assembly 3.

Figure 6A:
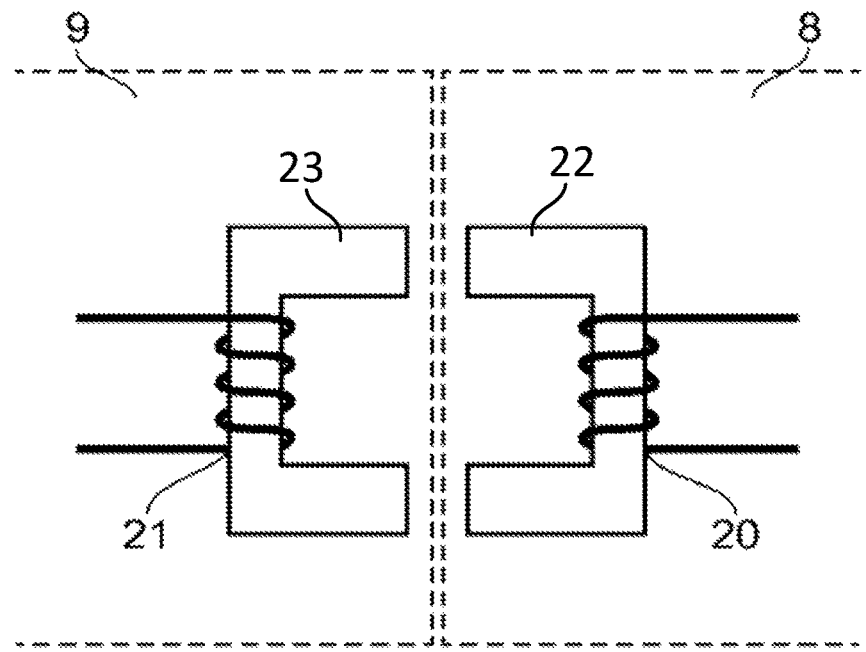
Figure 6B:
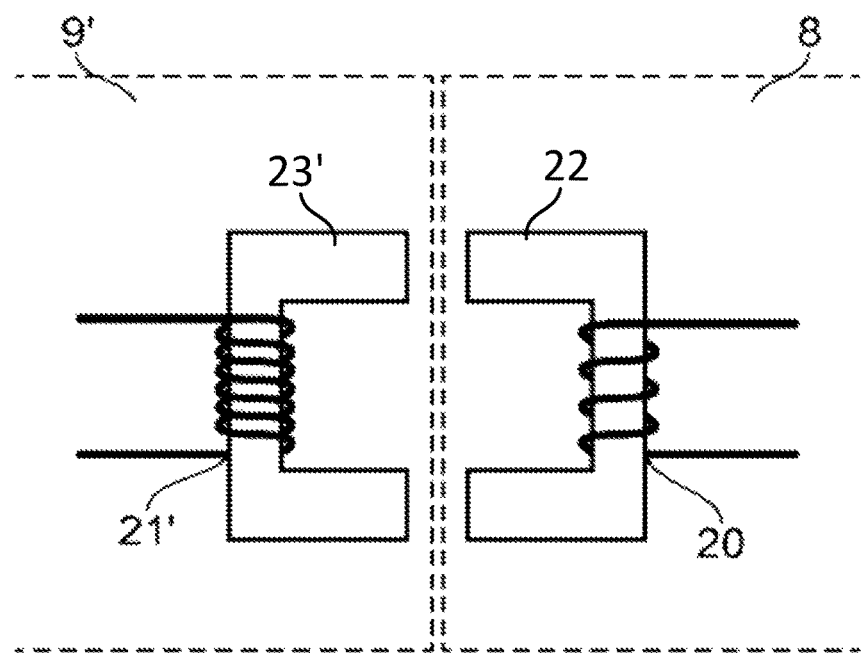

FIG. 6A shows an alternative embodiment in which the connector 8 on the handpiece 2 is provided with a primary winding 20 and a primary core 22, and the connector 9 on the electrode assembly 3 is provided with a secondary winding 21 and a secondary core 23. When the electrode assembly 3 is connected to the handpiece 2, the primary winding 20 and the secondary winding 21 together form a transformer output stage for the RF circuit 5. When the electrode assembly 3' of FIG. 2 is connected to the handpiece, the connector 9' has a secondary winding 21' with a different number of turns and a secondary core 23', as shown in FIG. 6B. In this way, the RF output reaching the end effector 11 is different from that reaching the end effector 11'. This is the case even if the original RF output produced by the handpiece is the same in both instances.

In this way, the voltage of the RF output supplied to the end effectors 11 & 11' is different, by virtue of the different secondary windings in each case. The RF output can therefore be matched to the particular electrode assembly used in conjunction with the handpiece 2, while maintaining the simplicity of the handpiece itself.

As an alternative to the primary winding 20 being present within the handpiece and the secondary winding 21 being present within the electrode assembly, both primary and secondary windings can be present within the electrode assembly, in which case the connections between the electrode assembly and the handpiece can be very straightforward, being simply power lines to provide power to the primary coil 20 in the electrode assembly.

Those skilled in the art will appreciate that the components present within the electrode assemblies, whether they are resistors, transformers, secondary windings or other components, can vary the output from the handpiece in order to customize it to the electrode assembly in question. The components can modify any one or more of a plurality of parameters associated with the output from the handpiece, including the power, voltage or current of the RF energy, the frequency of the RF energy, or the format (continuous or pulsed bursts, the signal shape (e.g. square wave, sinewave, sawtooth, etc), or the duty cycle) of the RF energy. Generally, therefore, embodiments of the present invention provide a handpiece which provides at least one common or standard RF output signal i.e. at a defined frequency and power and/or amplitude, and at least one electrode assembly that is adapted to fit onto the handpiece, and to receive from the handpiece the RF output signal and to adapt it to the specific signal required by the or each electrode assembly. As described, in embodiments of the invention the adaptation can be undertaken via components such as a step up or step down transformer, by networks of one or more passive components having resistive or reactive properties, or by other signal transformation means having the necessary transfer function.

Further modifications, whether by way of addition, deletion or substitution will be apparent to those skilled in the art to provide further embodiments, any and all of which are intended to be encompassed by the appended claims

The invention claimed is:

1. A handheld electrosurgical instrument comprising a handpiece and an electrode assembly, the electrode assembly including one or more electrodes and a connector by which the electrode assembly is capable of being attached and detached with respect to the handpiece, the handpiece including,
   a) a battery;
   b) an RF oscillator circuit for generating a radio frequency output;
   c) a switching device operable by a user of the handheld electrosurgical instrument;
   d) a primary transformer winding coupled to a first core; and
   e) a control circuit for controlling the radio frequency output, the control circuit being capable of receiving signals from the switching device and causing one or more radio frequency outputs to be supplied to the electrode assembly in response thereto;
   wherein the electrode assembly includes a secondary transformer winding coupled to a second core, such that when the electrode assembly is connected to the handpiece the primary and secondary windings are connected in order to act as a transformer to modify the radio frequency output from the RF oscillator circuit.

2. The handheld electrosurgical instrument of claim 1, wherein when the electrode assembly is connected to the handpiece the first and second cores are adjacent to each other.

3. An electrosurgical system comprising a handpiece and a plurality of electrode assemblies, the electrode assemblies being at least of a first type or a second type of electrode assembly, and each including one or more electrodes and being detachably connectible to the handpiece, the handpiece comprising
   a) a battery;
   b) an RF oscillator circuit for generating a radio frequency output;
   c) a switching device operable by a user of the electrosurgical system; and
   d) a primary transformer winding coupled to a primary core; and
   e) a control circuit for controlling the radio frequency output, the control circuit being capable of receiving signals from the switching device and causing one or more radio frequency outputs to be supplied to the electrode assembly in response thereto;
   wherein the first type of electrode assembly includes a first secondary transformer winding coupled to a first secondary core such that when the first type of electrode assembly is connected to the handpiece the primary transformer winding and the first secondary transformer winding are connected in order to act as a transformer to modify the radio frequency output from the RF oscillator circuit to produce a first radio frequency output at the first type of electrode assembly, and the second type of electrode assembly includes a second secondary transformer winding coupled to a second secondary core such that when the second type of electrode assembly is connected to the handpiece the primary transformer winding and the second secondary winding are connected in order to act as a transformer to modify the radio frequency output from the RF oscillator circuit to produce a second radio frequency output at the second type of electrode assembly.

4. The electrosurgical system of claim 3, wherein when the first type of electrode assembly is connected to the handpiece the primary core and the first secondary core are adjacent to each other, and when the second type of electrode assembly is connected to the handpiece the primary core and the second secondary core are adjacent to each other.

* * * * *